United States Patent [19]

Lapidus et al.

[11] Patent Number: 5,143,627
[45] Date of Patent: Sep. 1, 1992

[54] METHOD AND APPARATUS FOR PREPARING CELLS FOR EXAMINATION

[75] Inventors: Stanley N. Lapidus, Bedford, N.H.; Lewis T. Polk, Jr., Bedford, Mass.; Fredric L. Farber, Chestnut Hill, Mass.; J. Morgan Barlas, Malden, Mass.; Anne A. Hurley, Carver, Mass.

[73] Assignee: Cytyc Corporation, Marlboro, Mass.

[21] Appl. No.: 550,142

[22] Filed: Jul. 9, 1990

[51] Int. Cl.⁵ .................. B01D 37/00; B01D 33/00
[52] U.S. Cl. ............................ 210/767; 210/232; 210/241; 210/252; 210/321.68; 210/359; 210/398; 210/407; 210/784; 422/58; 422/72; 422/101; 436/177; 436/180
[58] Field of Search .................. 422/58, 72, 101; 436/177, 180, 63, 174; 210/85, 232, 241, 252, 359, 321.68, 398, 407, 767, 784, 803, 804, 780, 650; 435/311, 312, 240.25

[56] References Cited

U.S. PATENT DOCUMENTS

| | | | |
|---|---|---|---|
| 3,647,632 | 3/1972 | Johnson et al. | 210/360.1 |
| 3,900,290 | 8/1975 | Hornstra . | |
| 4,166,768 | 9/1979 | Tolbert et al. | 435/286 |
| 4,184,916 | 1/1980 | Tolbert et al. | 435/286 |
| 4,391,710 | 7/1983 | Gordon | 422/101 |
| 4,395,493 | 7/1983 | Zahniser et al. . | |
| 4,435,507 | 3/1984 | Stenkvist . | |
| 4,468,410 | 8/1984 | Zeya | 427/2 |
| 4,583,396 | 4/1986 | Hunt et al. . | |
| 4,647,376 | 3/1987 | Galaj | 210/321.68 |
| 4,670,147 | 6/1987 | Schoendorfer et al. | 210/541 |
| 4,755,300 | 7/1988 | Fischel et al. | 210/784 |
| 4,790,942 | 12/1988 | Shmidt et al. | 210/784 |
| 5,019,512 | 5/1991 | Varecka et al. | 435/286 |

FOREIGN PATENT DOCUMENTS

| | | |
|---|---|---|
| 1178183 | 11/1984 | Canada . |
| 0224962 | 6/1987 | European Pat. Off. . |
| 0244999 | 11/1987 | European Pat. Off. . |
| 0368621 | 5/1990 | European Pat. Off. . |
| 3338782 | 5/1985 | Fed. Rep. of Germany . |
| 63-202372 | 8/1988 | Japan . |
| 8909279 | 10/1989 | PCT Int'l Appl. . |

Primary Examiner—Robert A. Dawson
Assistant Examiner—Sun U. Kim
Attorney, Agent, or Firm—Lahive & Cockfield

[57] ABSTRACT

An apparatus and method provide automated collection and transfer of particles from a liquid suspension to a glass slide for visual examination. A solution which contains particles, for example cells, is drawn through a filter element so that particles too large to pass through the filter element collect against a first surface of the filter element. A transfer fluid, such as alcohol, is applied from a second surface of the filter element to the first surface, to transfer cells from the filter element to a glass slide positioned adjacent the filter element. An alternative transfer mechanism applies a selected pneumatic signal to the filter element for transferring collected cells to the viewing slide. The apparatus includes a device for dispersing the liquid suspension of particles prior to the collection process and particles collect against the filter element with a spatial distribution advantageous for visual examination. The transfer operation maintains this spatial distribution. The cell-dispersing device and the filter element are on a common structure, for unitary movement, and which is readily disposable and replaceable for each sample of particles.

36 Claims, 9 Drawing Sheets

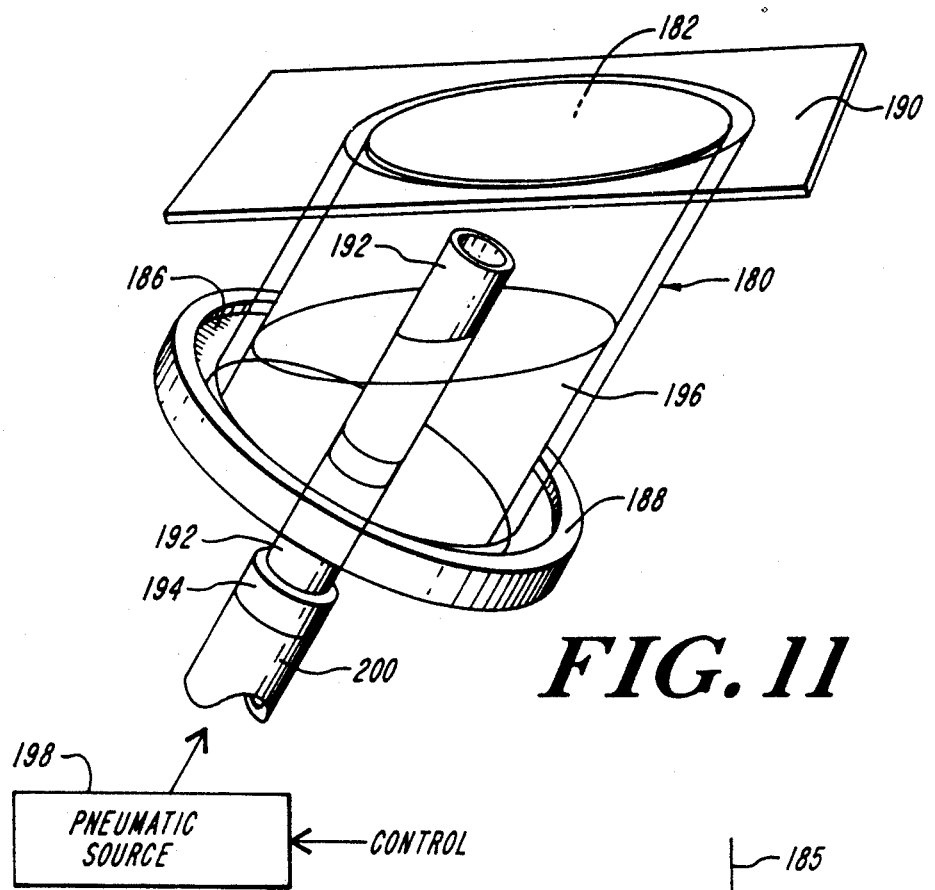
FIG. 11
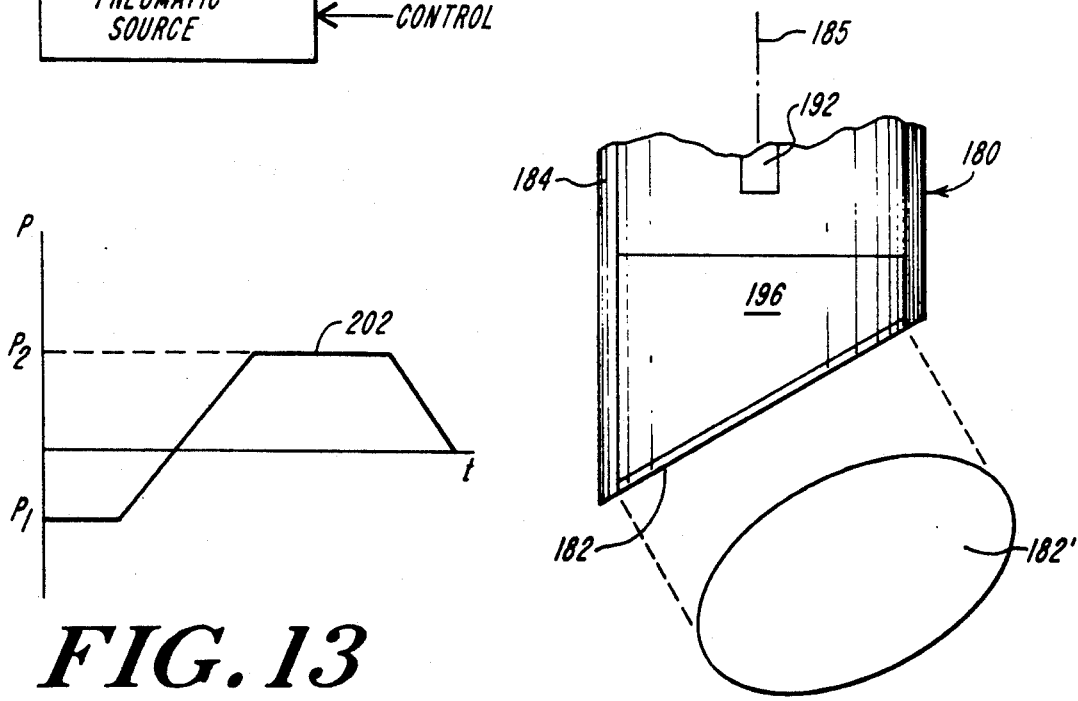
FIG. 13
FIG. 12

METHOD AND APPARATUS FOR PREPARING CELLS FOR EXAMINATION

BACKGROUND OF THE INVENTION

This invention generally relates to the field of article collection and transfer. The invention provides a method and apparatus for collecting a quantity of cells from a biological sample and transferring the cells onto a glass slide. The invention is useful in cytology, which is a medical and laboratory science that makes diagnoses based on findings in cells.

A typical cytological technique is a "pap smear" test, which is used in one instance to detect abnormal cells in a woman's cervix before they develop into cancer cells. The technique can also be used to aid in the detection of disease in other organs of the body.

Cytology is less invasive to a patient than traditional surgical pathological procedures, e.g. biopsy. All that is required for cytology is that a sample of cells be obtained from the patient, which can typically be done by scraping or swabbing an area, as in the case of cervical samples, by procuring fluids from body sites such as the chest cavity, bladder, or spinal canal, or by needle aspiration. After a solution containing cells is obtained using one of these techniques, the cells are collected from the solution and transferred onto a glass slide for viewing.

This processing of the cells typically requires that the cells be separated from one another, i.e. dispersed, so that individual cells can be transferred to the glass slide for visual examination. In addition, the dispersed cells are counted so that a generally known quantity of the cells can be transferred to the slide for the visual examination. The phrase "visual examination" is used herein in a broad context and includes human visual inspection as well as machine image inspection. It also includes inspection with various types of illumination. Also, practice of the invention can include procedures, such as staining, conventionally performed between collecting the cells and the actual examination.

It is important for effective visual examination that the cells have a proper spatial distribution. This enables individual cells to be examined. Ideally, this means that a single layer of cells is collected and transferred to the glass viewing slide.

Prior techniques for dispersing cells and for collecting a measured quantity of the cells; and for transferring them to an optical slide for visual examination, have several disadvantages. These include shortcomings such as requiring costly equipment, being time-consuming, requiring undue operator attention, being subject to inter-sample contamination, and providing limited performance in terms of reliability, repeatability, accuracy and precision. The prior techniques also present bio-hazard risks from the handling of the sample. These disadvantages are increasingly significant with the increasing use of cytologic diagnosis.

It is an object of this invention to provide an apparatus and method for quickly and efficiently collecting a selected quantity of dispersed cells from a sample solution. It is also an object of the invention to provide such an apparatus and method for transferring the cells onto a glass slide for visual examination with a uniform single-layer distribution.

A more specific object is to provide such a method and apparatus capable of automated operation with minimal operator attendance and yet with relatively high reliability, repeatability, accuracy, and precision as well as with low inter-sample contamination.

A further object is to provide such an apparatus and method that handle the specimen in a manner that presents low bio-hazard risks.

Another object of the invention is to provide such automated apparatus, for preparing cells for visual examination, that attains high inter-sample isolation with a minimal number of disposables and at relatively low cost.

Other objects of the invention will in part be obvious and will in part appear hereinafter.

GENERAL DESCRIPTION

An instrument according to this invention resolves problems associated with known equipment for collecting cells and other particles for cytology by providing a mechanism of relatively simple structure and operation that disperses particles in a liquid solution, collects an approximately known quantity of the cells from the solution, and presents the collected quantized cells, with a single layer spatial distribution, for transfer to a glass slide. The instrument can also transfer the cells, with the same distribution, to the glass slide. Another feature is that the instrument attains a cell distribution that is substantially uniform, and, further, that has a substantially uniform number of cells per unit area.

The instrument has a vial holder carried on a transport and that receives the specimen solution. A dispersing element is introduced to the sample liquid, preferably by operation of the transport. A preferred transport provides both lateral movement, for carrying the sample vial and a cell transfer mechanism from one location to another, and provides elevational vertical movement, as for introducing the dispersing element into the sample container and for removing it.

The dispersing element preferably subjects the cells in the sample liquid to shear forces, for dispersing clusters of cells. A preferred dispersing element produces the shear forces by mechanical agitation within the sample container. The embodiment described below employs rotary agitation, although other movements can be used, such as vertical or other reciprocation.

The instrument employs a collection vessel having a filter that is introduced to the sample liquid and onto which a selected quantity of the dispersed sample cells are collected. A pressure system connected with the collection vessel draws sample liquid into the vessel for collecting the cells on the filter surface.

The filter preferably is of the screen type in that it collects particles of a selected minimum size on a surface and allows filtrate to pass, e.g. a membrane filter. Cells of interest collect on the filter surface and blocks fluid flow through the filter. Accordingly, since there is no fluid flow through the filter in the area of collected cells, the cells collect in a single layer against the filter. The resultant spatial distribution of the cells collected on the filter facilitates effective visual examination of the cells transferred to the glass viewing slide.

A control system monitors this cell-collecting operation by monitoring parameters of the liquid flow to determine when a selected quantity of dispersed cells is collected on the filter.

An upper assembly of the instrument positions the filter device, with the collected cells on the filter surface, for abutment against an optical viewing support, typically a glass microscope slide. The upper assembly in one preferred form described below inverts the collection vessel, after removal from within the collection vial, and includes drain elements for draining liquid from within the collection vessel. A cell transfer mechanism brings an alcohol-bearing sponge into engagement with the back of the cell-bearing filter, and presses the cell-bearing filter against the glass viewing slide. This operation is coupled with an alcohol flow from the sponge, to release the cells from the filter and transfer them to the viewing screen. The cell transfer mechanism thus includes elements for pressing the sponge against the filter, flowing alcohol to the sponge, and collecting excess alcohol or other liquid released during the transfer operation.

An alternative embodiment employs a pneumatic mechanism for transferring the collected cells from the filter to the glass slide. The pneumatic cell-transfer mechanism preferably inverts the collection vessel, at least partially, to elevate the filter that carries the collected cells. After the cell-bearing filter is brought into abutment with the glass slide, a controlled pneumatic pressure, typically of clean air, is applied to the vessel interior. The pneumatic pressure tends to lift the collected cells off the filter, and presses them against the glass slide. This action transfers the cells, together with liquid in the filter pores, to the slide.

With this pneumatic cell transfer, the liquid that was previously aspirated into the collection vessel to collect the cells, can be retained in the vessel when it is inverted and when the cells transferred to the glass slide. The pneumatic transfer can thus be practiced without first draining this liquid from the vessel.

The pneumatic cell transfer mechanism accordingly preferably operates with a collection vessel structured to retain the cell-suspending sample liquid when it is re-oriented from the cell-collecting orientation for the cell-transfer operation. Further, a preferred practice of this embodiment of the invention employs a sample liquid having a selected level of alcohol that is transferred from the filter pores to the viewing slide concurrent with the pneumatic transfer of cells.

It is important to the method and apparatus of the invention that the cells maintain the spatial distribution with which they were collected on the filter, as they are transferred from the filter device to the glass slide. The invention thus provide cell collection and transfer that attains a single layer of cells on the glass slide. This facilitates examination of the cells, by ensuring an essentially unobstructed view of each individual cell.

A further feature of the invention is that the collection vessel that is fitted with the cell-collecting filter also performs as the dispersing agitator. This multiple function of the collection vessel minimizes the number of elements that are exposed to the cells of each sample.

An instrument according to the present invention preferably employs a fresh sample vial for each individual cell specimen, as well as a fresh filter-bearing collection vessel. It may also be desirable to provide a fresh cell-transferring sponge, where the instrument employs this element in the cell-transferring mechanism. An instrument according to the invention attains high inter-sample isolation upon simple replacement of only these two or three elements for each fresh sample, together with the selected collection and discarding of liquids used in the operation of the instrument. Moreover, the relatively simple operation, and the multiple functions which the instrument performs, minimize the requirements for operator attendance and time, as well as minimizing instrument maintenance and preparation.

The method and apparatus of this invention are well suited for practicing the invention described in the co-pending and commonly assigned application for patent, Ser. No. 487,637 and filed Mar. 2, 1990, entitled "METHOD AND APPARATUS FOR CONTROLLED INSTRUMENTATION OF PARTICLES WITH A FILTER DEVICE". The disclosure of that copending application is hereby incorporated by reference into this application.

One preferred instrument embodying this invention is prepared for use by clamping a sample vial, containing a specimen solution, onto a pedestal of a transport, and by installing a fresh collection vessel. Where used for the cell transfer operation, a fresh transfer sponge is installed. Typically, a clean glass slide is prepared to receive a quantity of cells collected from the specimen solution.

Once the instrument is prepared in this manner, the instrument subjects the sample solution to shear forces that disperse the specimen cells. This dispersion operation mechanically transforms clusters and most other aggregates of specimen cells to individual cells in liquid solution. The embodiment of this invention described below implements the dispersion operation by introducing a rotor, in the form of the collection vessel, into the sample vial and by spinning the rotor relative to the vial to subject the sample solution to shear forces.

The same collection vessel that functions as the disaggregation rotor is fitted with a screen type filter that is immersed in the sample solution for the disaggregation operation. With this structure, the instrument is automatically immediately ready, after the dispersion operation, for collecting dispersed cells on the filter by the controlled aspiration of the specimen solution into the collection vessel through the filter. In accordance with the teaching in the above-identified copending application, the sample solution is drawn through the filter to collect cells on the filter. After a predetermined quantity of the cells is collected in this manner, the transport mechanism removes the collection vessel from the sample vial, illustratively by lowering the sample vial. As a result, the lowered vial is out of the way of subsequent operations, and is readily accessible for removal and replacement.

During the next phase of operation, with one embodiment described below, the instrument partially inverts the collection vessel, with the cell-bearing filter initially at its lower end and with the vessel partially filled with aspirated solution, for draining the solution through a drainage port to a waste conduit. The instrument then further inverts the now-drained collection vessel to place the filter facing upward.

A stopper cap, which heretofore has sealed the collection vessel and which is fitted with one or more ports for connection with pressure control elements, is separated from the collection vessel and removed to provide clearance for a cell-transfer mechanism to enter the collection vessel. The transport transfers the cell-transfer mechanism into alignment with the inverted collection vessel. The cell-transfer mechanism deploys a sponge against the filter, on the side opposite the cell-bearing side, and directs a low pressure flow of alcohol into the sponge. The pressure of the alcohol-bearing sponge against the filter and the excess alcohol cause the collected cells to adhere to a glass viewing slide abutted against the cell-bearing surface of the filter. The cells thus adhere to the viewing slide and are fixed to it, and hence are ready for staining and inspection. The cells have the same spatial distribution on the viewing slide as they had on the filter, which is desirable for visual examination.

The instrument has now completed the transfer of a selected quantity of dispersed cells to the viewing slide, from the sample of aggregated cells initially presented to it in the sample vial. The instrument is ready to return to starting position and be fitted with a clean sponge and fresh collection vessel for processing a fresh sample.

Alternative to the foregoing embodiment that transfers collected cells with an alcohol liquid mechanism, another embodiment described in detail below transfers the collected cells with a pneumatic action. The operation of this embodiment proceeds from collecting cells on the filter of the collection vessel to transferring them to a viewing slide by disposing the cell-bearing filter of the collection vessel adjacent the viewing slide. The collection vessel typically continues to contain the liquid aspirated during the cell-collection operation.

A pulse of clean air or other gas is directed into the collection vessel to deflect the screen filter outward relative to the vessel and into abutment with the glass slide, and to dislodge collected cells from the filter and against the slide. The air pulse also blows liquid from the pores of the filter onto the slide, and thereby wets the slide. The liquid preferably has a selected alcohol content and pH, to enhance the cell transfer and the cell viability on the slide.

In a preferred practice of this pneumatic cell transfer, the collection vessel is inverted or otherwise oriented to dispose the cell-bearing filter surface upward, for abutment against the underside of a viewing slide.

The actions of the air pulse are to deflect the screen filter against the slide, to dislodge cells from the filter surface and onto the slide, and preferably also to blow liquid out from the filter pores and onto the slide. It is deemed advisable that the pressure of the air pulse be below the bubble burst point; a pressure below five psi and typically in the order of two psi is deemed preferable.

In one specific practice of the invention, the air pulse drives the pressure in the inverted collection vessel from the negative pressure used for the aspirating, cell-collecting operation, to a positive pressure below the bubble pressure, and has a duration in the order of two to five seconds.

It is one feature of the invention that cells and other particles, as collected and presented in liquid preservative solution, are prepared for examination and applied to a viewing slide with minimal processing. The attainment of this minimal processing results in a simple mechanism, ready automation, minimal operator attendance, and minimal risks of intersample contamination and of bio-hazards from the sample material.

The apparatus and method of the invention attain the foregoing minimal processing operation by dispersing the cells directly in the original sample vial, i.e. without transfer to another container structure. Further, the dispersed cells are collected with quantizing, to collect the desired quantity of cells, directly from the same sample container. This operation includes immersing a screen filter into the sample in the vial and aspirating liquid through the filter for collecting cells directly from the vial onto the filter surface.

In further accordance with the invention, the cells are carried on the filter for transfer directly to the viewing slide. As mentioned, the cells are collected on the filter and transferred to the viewing slide while maintaining a proper spatial distribution which ensures that essentially only a single layer of cells resides on the viewing slide.

The method and apparatus of the invention can thus be practiced without flowing sample cells through a conduit and without transfer from one container or holder to another, aside from the foregoing transfer from the initial sample vial to the filter for subsequent transfer to the viewing slide.

It is also a feature of the invention to provide a low cost disposable element for a cell processing instrument which functions both to cells and to collect a selected quantity of the dispersed cells with a desired spatial distribution, all within the same containment of the sample cells.

More particularly, it is a feature of the invention to provide a device for immersion in a cell suspending liquid and for agitation relative to the liquid to produce shear forces in the liquid which disperse the sample cells. It is a further feature that the device includes a screen filter element through which the cell-suspending liquid can be drawn for collecting sample cells on a surface of the filter element. The filter element has a porosity for blocking the sample cells of interest and for freely passing the cell-suspending liquid and smaller particles, i.e. particles, such as red blood cells, smaller than the cells of interest. A further feature is that the dispersing and collecting device collects the cells thereon for direct transfer onto a cell-examining slide element. Further, the device accomodates this transfer with the transferred cells having substantially the same spatial distribution on the slide element as they had on the device. A preferred configuration of the screen filter element for this collection and transfer is that it be planar.

Yet another feature of the invention is that the cell dispersing and collecting device be removably and replaceably mountable in a mechanism for the selective immersion in the cell-suspending liquid to implement the foregoing cell dispersion, quantized collection and subsequent transfer operations.

A cell dispersing and collection device for practice of the invention, in one preferred form, has a liquid containment body formed at least in part with a screen filter element through which liquid can flow into and out of the containment body, and with a selected porosity. The liquid containment body is arranged for agitation, relative to a selected axis, and relative to a cell-suspending liquid, for subjecting the cells suspended in the liquid to shear forces for dispersing the cells. The device further has a mounting structure for removably and replacably mounting it, with selected orientation and with selected disposition of the liquid containment body and of the filter element. The mounting structure in one preferred embodiment includes a rim connected for mountingly supporting the containment body and concentric with the agitation axis. The rim is further arranged for both removably and replacably mounting the containment body and for receiving an agitating movement for providing the foregoing agitation of the body relative to that axis. A preferred dispersing agitation of the collection vessel is rotation, about the selected axis.

The dispensing and collecting device further has at least one port or conduit communicating with the liquid containment body for applying a controlled pressure condition to the filter element. It is preferred that the vessel body and filter element are part of a fluid confining vessel. In one embodiment, the vessel can be selectively opened and closed, for draining liquid therefrom and, alternatively, for containing liquid, respectively.

In another embodiment, the conduit extends a selected distance within the vessel, from a side opposite the filter element, for extending upward through a selected volume of liquid contained within the vessel below the filter element, when the vessel is oriented with the filter element uppermost. In this orientation, the conduit enables selected pneumatic conditions to be applied within the vessel directly to the filter element, without the prior drainage of liquid from the vessel and without bubbling the pneumatic fluid through that liquid.

As described, the invention offers significant advantages over known methods of collecting and transferring cells by performing the majority of the required steps automatically. A technologist utilizing the apparatus of the invention need only set the unit in its starting position by providing it with a fresh collection vessel and a sample, and with a fresh transfer sponge, where used. Then, by merely activating the apparatus, a sample of cells will be collected from the solution and transferred to a glass viewing slide so that the necessary diagnosis can be performed.

These and other advantages of the invention will be more fully understood by reference to the following detailed description, in conjunction with the accompanying drawing in which like reference numbers refer to like elements and in which:

FIG. 11 is a fragmentary side elevation view of another instrument according to the invention during a cell-transfer operation;

FIG. 12 is a simplified fragmentary side elevation view of the collection vessel of FIG. 11 disposed for a cell-collecting operation; and FIG. 13 is a graph of pressure as a function of time illustrating one part of the instrument operation in accord with the invention.

DESCRIPTION OF ILLUSTRATED EMBODIMENT

Figure 1:
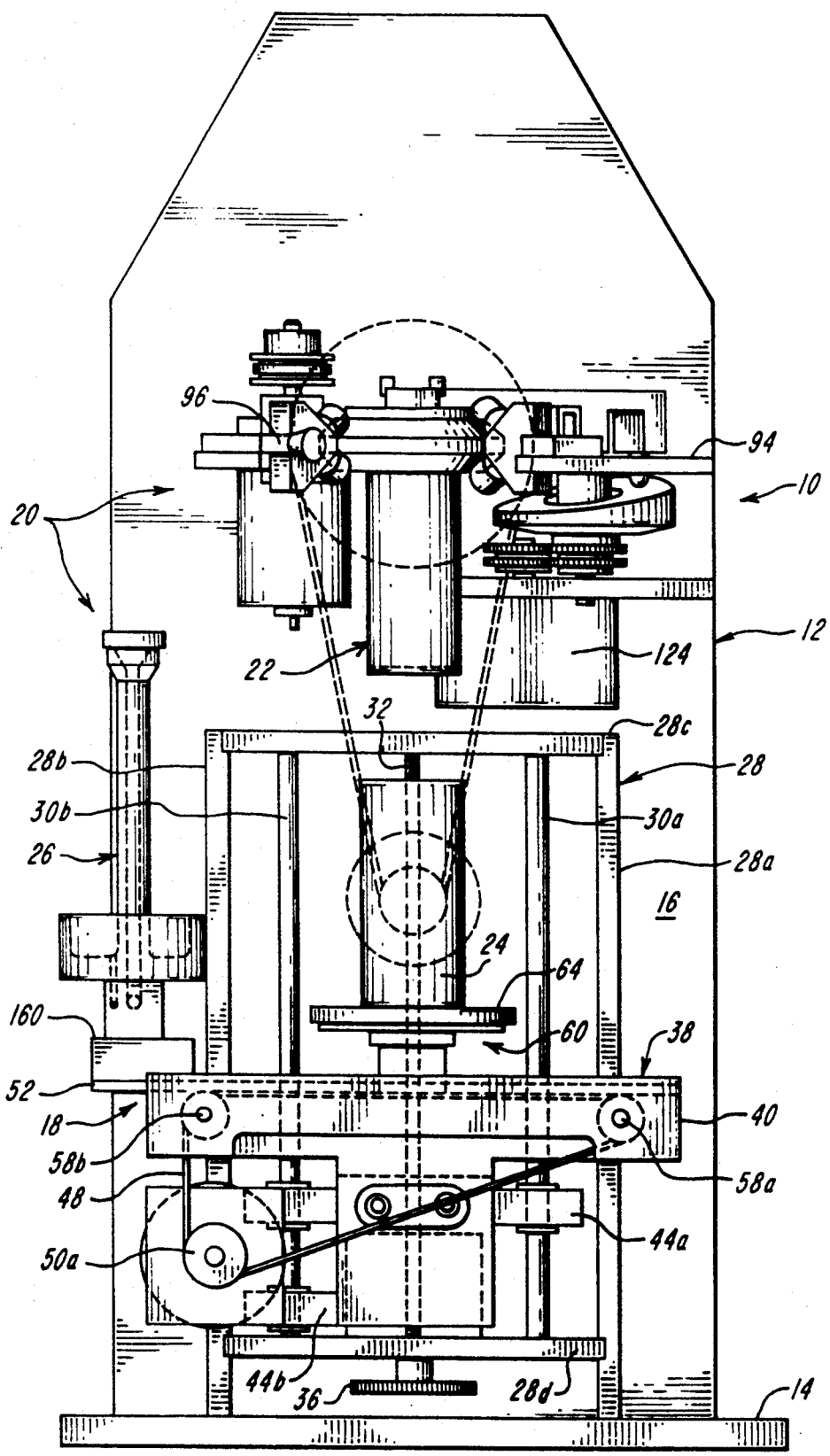
FIG. 1 is a front view of an instrument in accordance with the invention, in its starting position.
Figure 4:
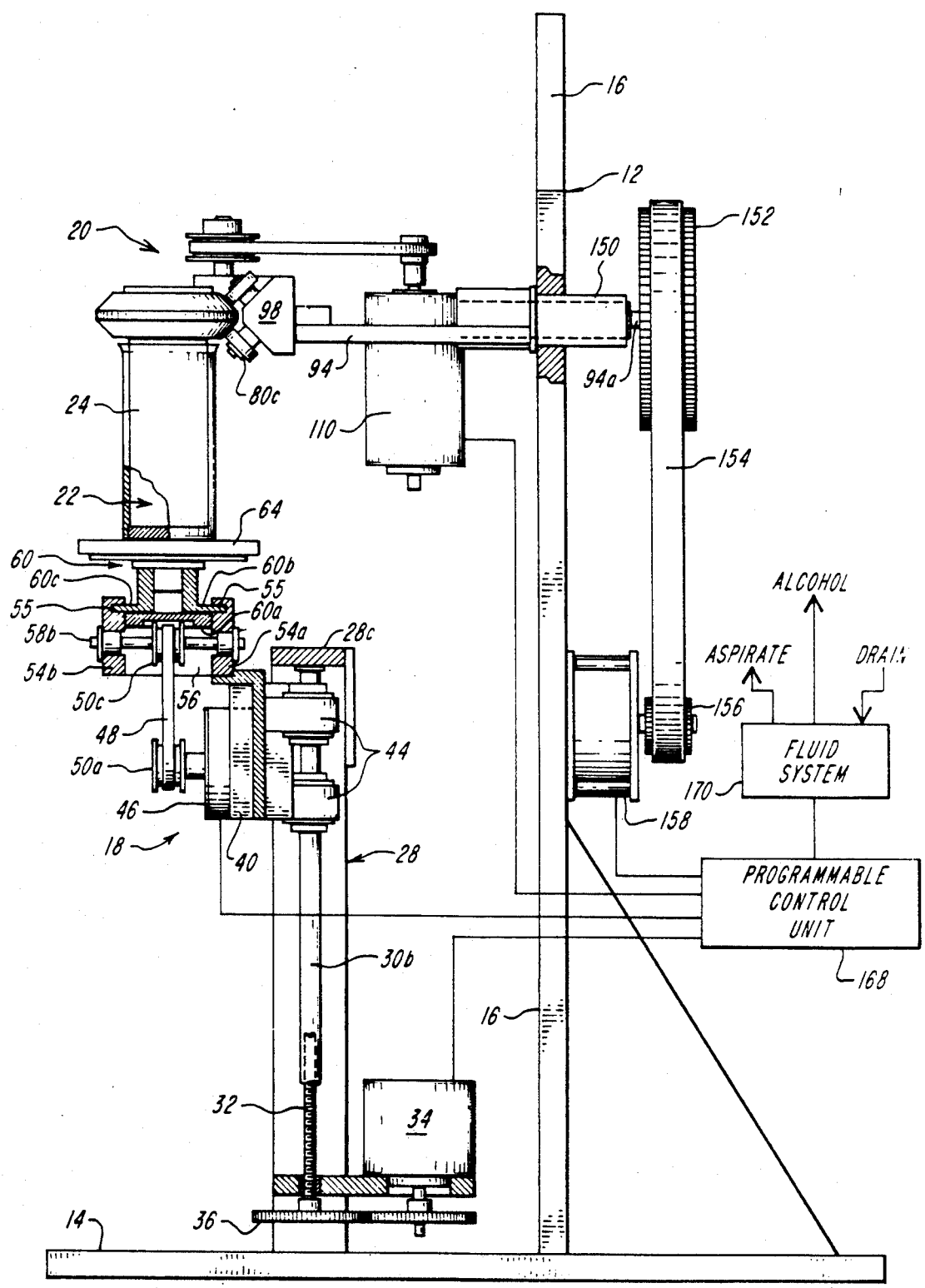

An instrument 10 according to the invention has, as shown in FIGS. 1 and 4, a housing 12 having a base 14 that mounts an upright panel 16.

Two major portions of the instrument are a transport mechanism 18 mounted on the housing 12 and a transfer mechanism 20, also mounted on the housing. The instrument operates with a disposable sample collector 22 that mounts with the transfer mechanism 20.

The illustrated transport mechanism 18 selectively positions a removable and replaceable sample container 24, and a sample transfer device 26 that is part of the instrument. The transport mechanism 18 provides both vertical movement, between a lower-most position shown in FIG. 1 and an upper-most position shown in FIG. 3, and horizontal movement between a left most sample-collecting position shown in FIG. 1 and a right-most sample transferring position shown in FIG. 10.

The illustrated transport mechanism 18, as shown in FIGS. 1 through 4, has an upright frame 28 that mounts on the housing base 14 and that supports two vertical, side-by-side guide posts 30a and 30b and a lead screw 32. The illustrated lead screw extends vertically, parallel to the guideposts 30a and 30b, and is centrally disposed between them. An electric motor 34, secured to the housing 12 by way of the frame 28 as shown in FIG. 4, drives the lead screw in either direction by way of a gear train 36. The illustrated frame 28 has uprights 28a and 28b mounted on the base 14, an uppermost horizontal beam 28c, and a lowermost horizontal beam 28d. The guide posts 30a and 30b, and the lead screw 32 are illustrated extending between the beams 28c and 28d.

An elevator 38 of the transport mechanism 18 has a horizontal lift platform 40 slidably mounted on the guideposts 30a and 30b. The lift platform is threadably engaged with the lead screw 32 to be vertically positioned, i.e. moved on the guide posts, by rotation of the lead screw between the raised position of FIG. 3 and the lower position of FIG. 1. The illustrated lift platform 40 mounts two sets of slide bearings 44a and 44b, each of which slidably seats on one guidepost 30a, 30b, respectively. The lift platform 40 also mounts an electric motor 46. The motor drives a sheave 50a drivingly engaged with a belt 48 that is engaged with sheaves 50b and 50c on a slide mechanism 52. The illustrated slide mechanism 52 is mounted on the lift platform 40 and is disposed generally above and parallel to it.

As further shown in FIGS. 1 through 4, the illustrated slide mechanism 52 mounts a carriage 60 on a pair of slide tracks 54a and 54b. The back slide track 54a is mounted to the lift platform 40 and the front slide track 54b is spaced forward of and parallel to the rear slide track 54a by a set of three spacer blocks 56. The slide tracks are recessed with opposed and parallel track slots 55.

Parallel and horizontally extending shafts 58a and 58b are rotatably mounted to span between the slide tracks 54a and 54b at the left and right ends of the horizontally-extending tracks, as appears in FIG. 1. Each shaft 58a and 58b mounts one idler sheave 50b, 50c spaced between the slide tracks.

Figure 10:
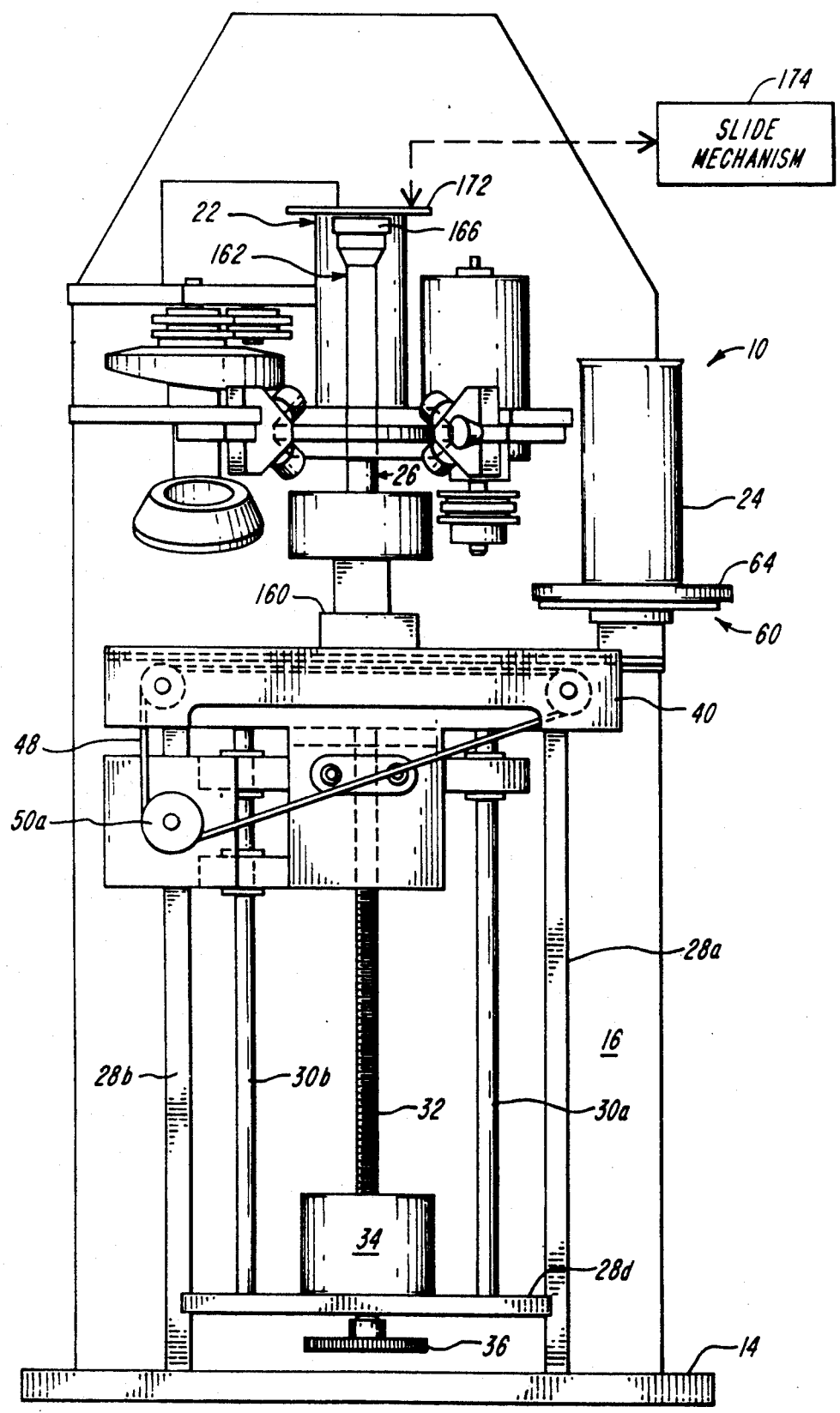
FIG. 10 is a front view of the instrument of FIG. 1 in a cell transfer position.

The carriage 60 of the transport mechanism 18 is carried on the slide mechanism 52 and engaged with the belt 48 for horizontal sliding movement between the sample collection left-most position of FIG. 1 and the sample transfer, right-most position of FIG. 10. The illustrated carriage 60 has a base 60a slidably seated between the slide tracks 54a and 54b adjacently above a horizontal span of the belt 48 as it passes between the idler sheaves 50b and 50c. The carriage base is secured to the belt and accordingly moves back and forth with movement of the belt 48.

The carriage 60 has a pair slide rails 60b and 60c secured to the base 60a and each of which slidably seats in one track slot 55. The rear and forward carriage slide rails 60b and 60c, each slidably engaged in the slot in one slide track 54a and 54b respectively, carry a sample holder 64 and the transfer mechanism 20, to move these elements between the sample collection position shown in FIG. 1 and the sample transfer position shown in FIG. 10. The sample holder 64 receives the sample container 24 and preferably is fitted with a releasable and re-engagable holding mechanism (not shown) for selectively positioning the sample container 24 on the instrument 10 and for holding it essentially stationary on the carriage 60.

During operation, the instrument 10 immerses the sample collector 22 into a liquid sample in the sample container 24, and collects on the collector 22 a selected quantity of sample cells from the sample liquid. The instrument then removes the sample collector 22 from the sample liquid for transferring the collected cells to a glass viewing slide, as described below.

Figure 2:
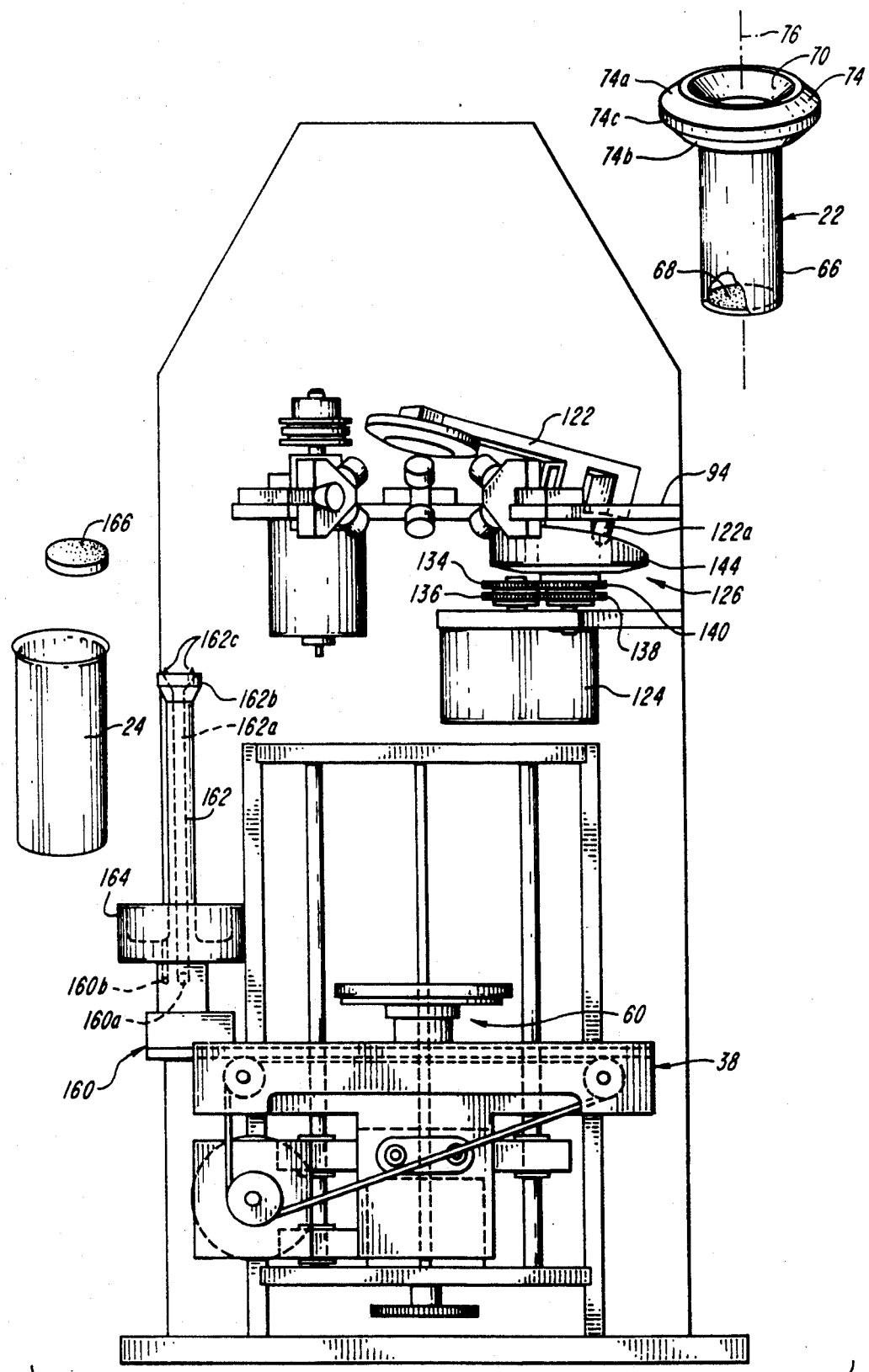
FIG. 2 is a view similar to FIG. 1 with disposable elements and an accessory sample container removed.
Figure 5:
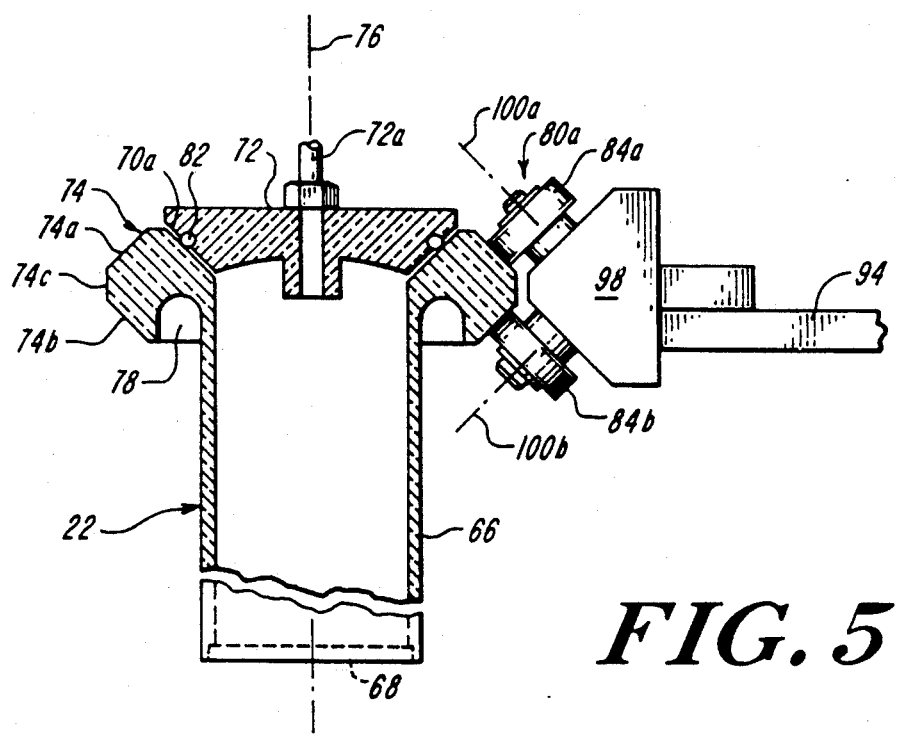
FIG. 5 is a side view, in partial cross-section, of a collection vessel and rim guide for use with the instrument of FIG. 1 in accordance with a preferred embodiment of the invention.

As shown in FIGS. 2 and 5, the illustrated sample collector 22 is a vessel with a cylindrical outer wall 66 closed at one axial end by a screen filter 68, preferably a membrane filter. The other axial end of the cylindrical wall 66 is open and has an aperture seal 70 that sealingly engages a cover 72, as shown in FIG. 5 and 6, to close the sample collector.

As further shown in FIGS. 2 and 5, the illustrated sample collector 22 has a rim 74 at its aperture end, i.e. distal from the filter 68, and projecting radially outward from the cylindrical wall 66 for removably and replacably mounting the sample collector 22 with the instrument 10, and for drivingly rotating it about the central axis 76 of the cylindrical wall 66.

Figure 6:
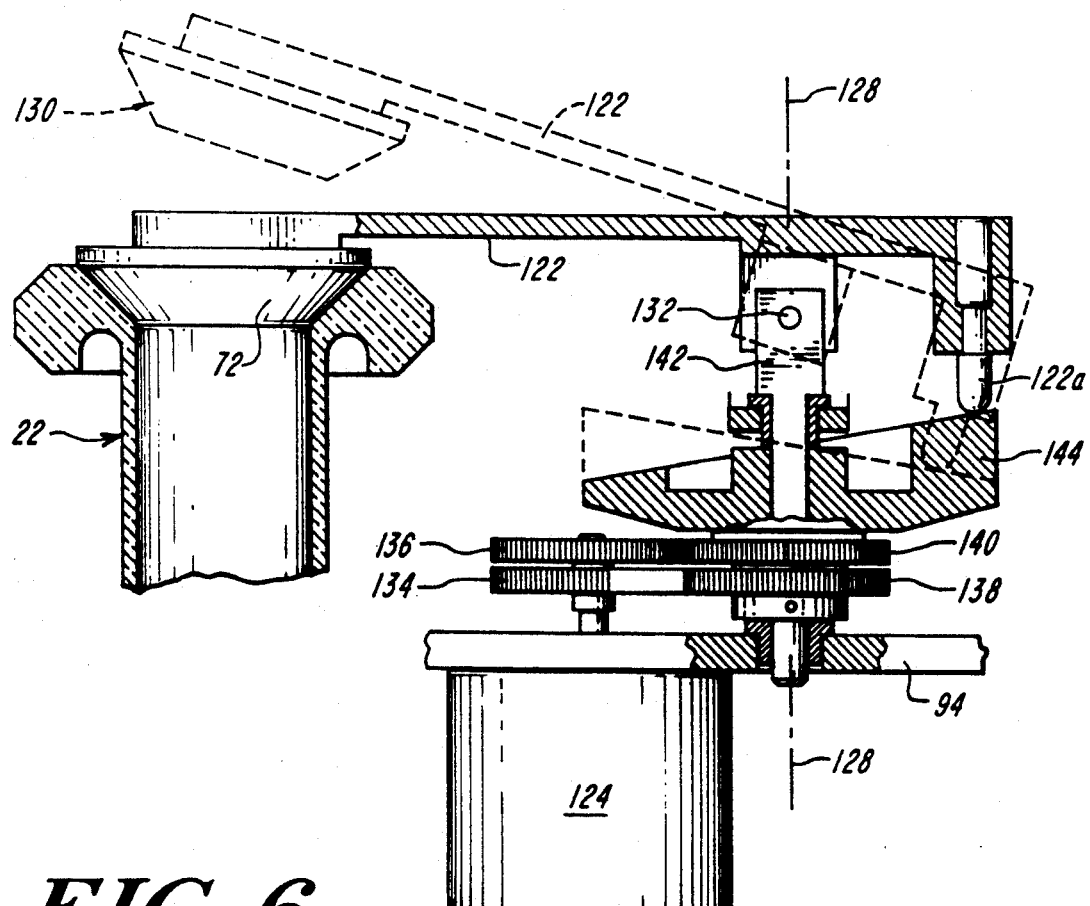
FIG. 6 is a side view, in partial cross-section, of a stopper arm actuation assembly in accordance with a preferred embodiment of the invention.

The sample collector 22 further has a liquid collecting trough 78 at its normally upper end, as appears in the normally upright orientation of the collector 22 shown in FIGS. 5 and 6. The illustrated trough 78 is formed in the underside of the rim 74 outside the cylindrical wall 66 and facing normally downward.

Figure 9:
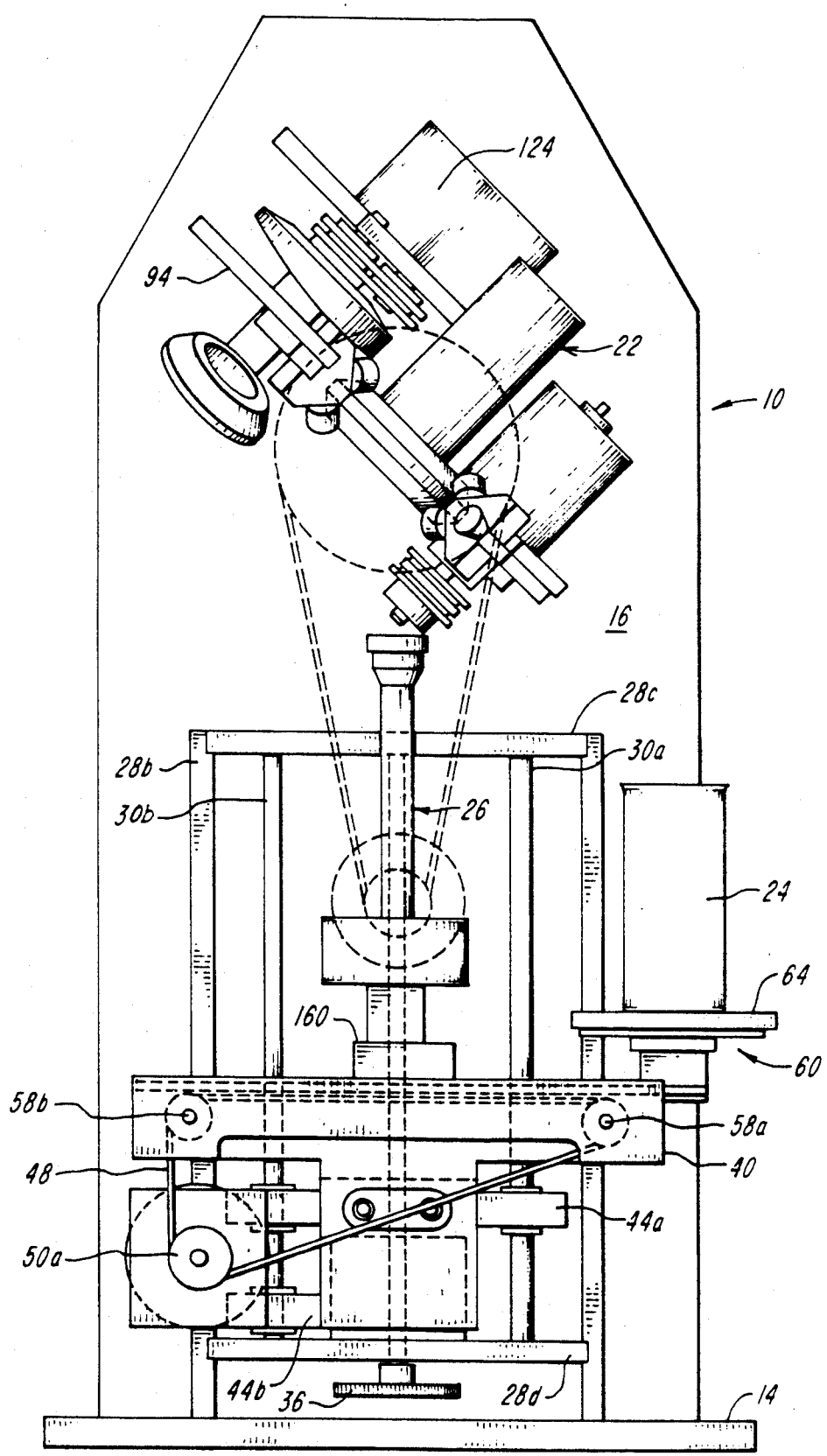
FIG. 9 is a front view of the instrument of FIG. 1 in a collection vessel-draining position.

The illustrated rim 74 has upper and lower flange surfaces 74a and 74b, each orientated at 45° relative to the axis 76 to the define a right angle between them, for engaging a triad of idler roller pairs 80a, 80b and 80c, as FIGS. 5 and 9 show. This engagement of the rim, with the three equally-spaced roller sets, selectively locates and orientates the sample collector 22 in the instrument 10. The outer-most surface portion of the illustrated rim 74 is a cylindrical drive surface 74c that is coaxial and concentric with the cylindrical wall 66. With this illustrated construction, a radial cross-section through the rim 74, as appears in FIG. 5, has the flange surfaces 74a and 74b disposed as sides of an equilateral triangle that is truncated at its apex by the drive surface 74c.

The illustrated trough 78 is an axially-extending annular recess in the rim 74 at the normally lower flange surface 74b, as also appears in FIG. 5.

The illustrated aperture seal 70 of the sample collector 22 is an outwardly flaring 45° beveled surface concentric with cylinder wall 66 about the axis 76 and thus extends parallel with the rim flange surface 74b. The aperture seal 70 sealingly engages a matingly flared surface 72a on the cover 72, which preferably carries an O-ring sealing member 82 on the sealing surface 70a.

With further reference to FIGS. 2 and 5, the screen filter 68 is preferably a membrane type filter having a porosity to block sample cells that are to be collected and to pass smaller cells and other particles, as well as the cell-suspending liquid, relatively freely. In one illustrated preferred embodiment, the filter 68 is a polycarbonate membrane having a porosity of 5 micrometers, as marketed by Nuclepore Corporation, in Pleasanton, Calif., U.S.A.. The filter is bonded to the lower end of a cylindrical outer wall 66 having an outer diameter of one inch concentric with a cylindrical inner diameter of 0.84 inch, and having an axial length of 2.2 inches. The rim 74 and the aperture seal 70 and the cylindrical outer wall 66 are of materials inert to the sample and other liquids to be encountered.

Figure 3:
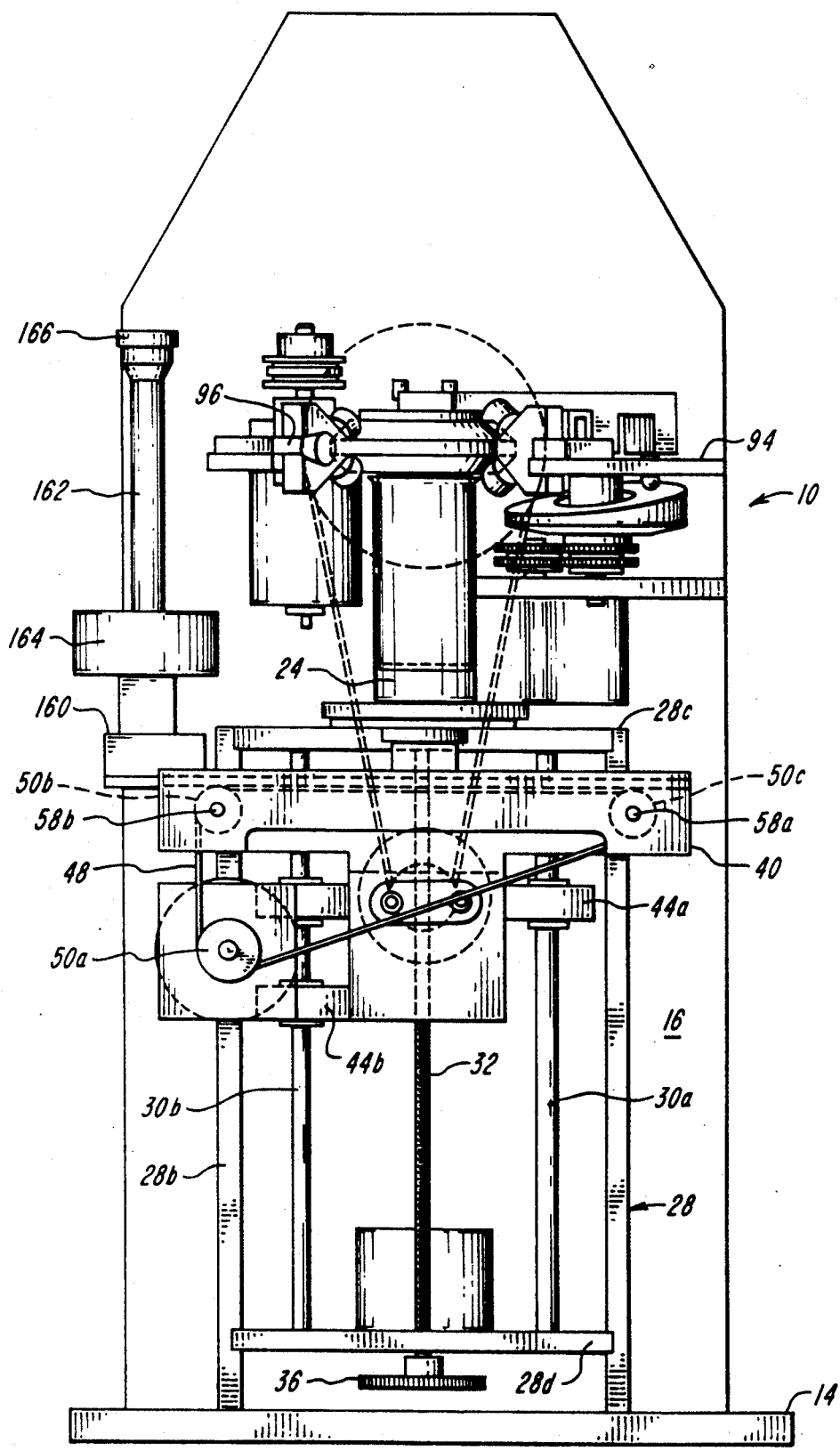
FIGS. 3 and 4 are, respectively, front and side elevation views of the instrument of FIG. 1 in the cell-collection position.

The outer diameter of the sample collector outer wall 66 is dimensioned to telescopically fit within the sample container 24, as shown in FIGS. 3 and 4, with a selected radial clearance therebetween. Further, rotation of the collector 22 relative to the sample container 24, when in this telescopically inter-fitting position, subjects liquid in the container 24 to shear forces that disperse cells in the sample liquid. The sample collector 22 thus has one function as a dispersing rotor, for separating sample cells suspended in the liquid in the sample container 24.

A second function of the sample collector 22 is to collect sample cells on the outer surface of the screen filter 68. The instrument 10 performs this operation by aspirating sample liquid into the collector 22 from the sample container 24 in which the collector is immersed.

The transfer mechanism 20 of the instrument 10, which mounts and positions and drives the sample collector 22 for the forgoing cell-dispersing and sample-collecting functions, as well as for the transfer of collected cells to a viewing slide, has three functional portions. One is a holder for mounting the sample collector 22 and is formed with the set of roller pairs 80a, b, c and a second is the cover 72 for selectively closing the sample collector 22. The third is a multiple-axis manipulator that selectively spins and orients a sample collector 22 mounted with the holder.

Figure 7:
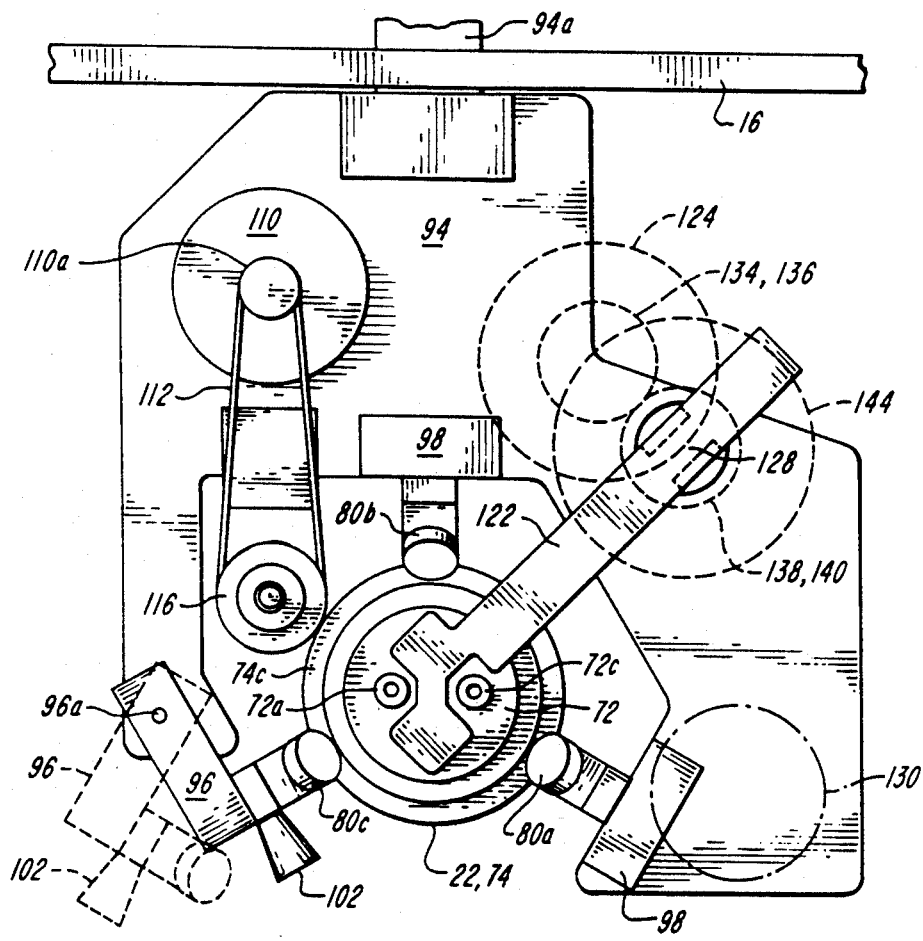
FIG. 7 is a side view of a collection vessel drive assembly for the instrument of FIG. 1 in accordance with the present invention.

The holder portion of the transfer shown in FIGS. 1 and 7, removably and replacably mounts the sample collector 22 to the instrument 10 by means of the set of three roller pairs 80a, 80b, and 80c arranged to engage the sample collector rim 74 at three equally spaced locations about the circular periphery of the rim. Roller pairs 80a and 80b are fixedly mounted to a manipulator plate 94, as appears in FIGS. 1, 4, and 7. A hinged release arm 96 mounts the third roller pair 80c to the manipulator plate 94. Each roller pair 80 has a pair of positioning rollers 84a and 84b, each freely rotatable about its axis, and mounted to a block 98. The block 98 of each roller pair 80a and 80b is fixedly mounted to the manipulator plate 94, as shown in FIGS. 5 and 7. As appears in FIG. 5, the upper roller 84a of each pair 80 rotates about an axis 100a extending 45° above the plane of the plate 94, and the lower roller 84b rotates about an axis 100b extending 45° below that plane. The two rollers of each pair 80 thus define a substantially right included angle between them and engage the upper and lower rim flange surfaces 74a and 74b, as FIG. 5 shows, for seatingly locating the collector 22 and for supporting it for rotation about its central axis 76.

With further reference to FIG. 7, the release arm 96 that mounts the roller pair 80c mounts the block 98 at an outer end, from which a handle 102 extends. The release arm is rotationally mounted at its other end to the manipulator plate 94 for rotation about an axis 96a transverse to the plane of plate 94. A spring resiliently biases the arm counter-clockwise about the axis 96a (FIG. 7)

into engagement against the collector rim 74. The release arm 96 is thus rotatable from the holding position shown in solid lines in FIG. 7 to the release position shown with dash lines in FIG. 7, where the sample collector 22 can readily be removed from the instrument and conversely can be installed. The spring bias and rotational mounting of the release arm 96 with the plate 94 preferably provide an over-center or like operation that maintains the arm in the open position, and that otherwise resiliently drives it to the closed position.

Figure 8:
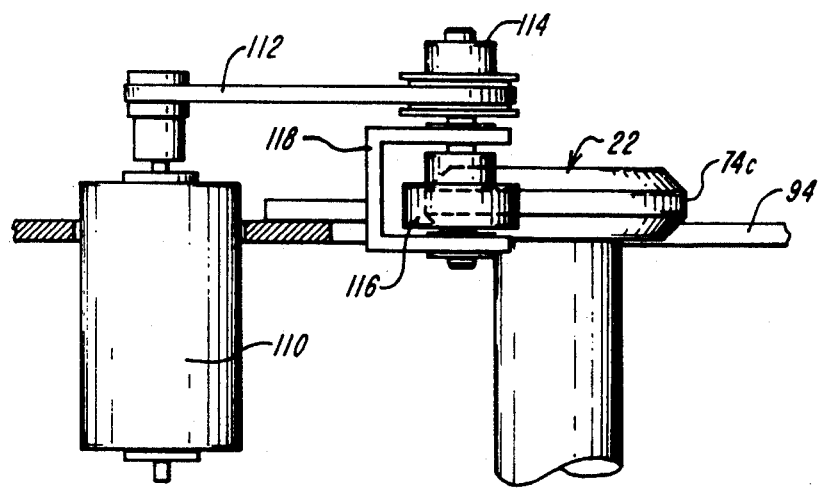
FIG. 8 is a top view of an upper support plate assembly of the instrument of FIG. 1 in accordance with a preferred embodiment of the invention.

The manipulator portion of the transfer mechanism 20, as shown FIGS. 7 and 8, has a motor 110 mounted on the manipulator plate 94. The motor shelf carries a sheave 110a engaged with a belt 112. The belt 112 is engaged with a spindle 114 that carries a rim-drive wheel 116. The drive wheel 116 drivingly engages the drive surface 74c on the rim 74 of the sample collector 22. A bracket 118 fastened to the manipulator plate 94 mounts the spindle 114 for rotation about the spindle axis, which is parallel with axis of motor 110 and with the axis 76 of a sample collector 22 mounted in the holder formed by the roller pairs 80a, 80b and 80c.

Another part of the manipulator portion of the instrument transfer mechanism 20 is the cover 72, which is shown closed with a sample collector 22 in FIG. 5 and open from the sample collector in broken lines in FIG. 6. As shown in FIGS. 6 and 7, the cover 72 is carried on an arm 122 that can rotate about a swing axis 128 and that can rotate about a lift axis 132. A motor 124 mounted to the manipulator plate 94 drives the arm 122 by way of a gear and cam mechanism 126. The lift axis 132 extends parallel with the plane of the manipulator plate 94 and the swing axis 128 extends transverse to that plane.

The motor 124 and the gear and cam mechanism 126 provide the following operation, starting with the arm 122 and the cover 72 in an initial open and displaced position 130 shown with broken lines in each of FIGS. 6 and 7. Upon rotation of the motor 124, the gear and cam mechanism 126 rotates the arm 122 from the initial position 130 and about the swing axis 128, without rotation about the lift axis 132 so that the cover remains in the raised position shown in broken lines in FIG. 6, to a closed or sealing position, shown in solid lines in FIG. 7, where the cover overlies the open end of the sample collector 22. Upon further rotation of the motor 124, the gear and cam mechanism 126 do not rotate the arm 122 further about the swing axis 128, and rotate the arm only about the lift axis 132 for moving the cover from the raised position shown dotted in FIG. 6 to the closed position shown there in solid lines.

In response to opposite rotation of the motor 124, the gear and cam mechanism 126 successively raises the arm 122 about the lift axis 132 from the closed position shown solid in FIG. 6 to the raised position shown there in broken lines, without rotation about the swing axis 128. Continued reverse rotation of the motor 124 causes the gear and cam mechanism 126 to maintain the arm 122 with the cover raised, i.e. with no further movement about the lift axis 132, and to rotate the arm only about the swing axis from the closed position to the initial displaced position 130, FIG. 7.

The illustrated construction of the gear and cam mechanism 126 for this operation employs a pair of stacked concentric gears 134 and 136 on the shaft of motor 124, which is parallel to and displaced from the swing axis 128 as appears in FIG. 7. A further pair of stacked concentric driven gears 138 and 140 is concentric with the swing axis 128. The motor gear 134 engages the driven gear 138, which is keyed to rotate a swing shaft 142, to which arm 122 is mounted for concurrent rotation about the swing axis 128 and for independent rotation about the shaft axis 132. One of the gears 134 and 138 has teeth on only a selected segment. The provision of teeth on only a segment of one of the gears 134, 138 causes them to rotate the arm 122, by rotation of the swing shaft 142 and about the swing axis 128, during only a selected portion of motor rotation, i.e. for shifting the arm 122 between the displaced open and the closed positions shown in FIG. 7.

The other motor gear 136 engages the driven gear 140, which in turn rotates a cam plate 144. An extension of the arm 122, beyond the rotational engagement with the swing shaft 142 and distal from the cover 72, forms a cam follower 122a that slidingly engages the contoured surface of the cam plate 144. The cam plate 144 is contoured to move the cam follower 122a vertically relative to the showing in FIG. 6, for opening and conversely closing the cover 72, during selected rotation. At other rotational positions, the cam plate surface holds the cam follower stationary, for maintaining the cover raised open or lowered shut. A spring mechanism (not shown) is coupled with the arm 122 to resiliently bias it to the raised position. Accordingly upon rotation of the cam plate 144 to the dotted position shown in FIG. 6, the resiliently-acting spring moves the arm 122 to the raised position, thereby removing the cover away from the sample collector 22.

FIGS. 4 and 7 show that the manipulator portion of the instrument transfer mechanism 20 further includes a rotational mounting of the manipulator plate 94 to the housing panel 16. A bearing 150 rotationally mounts the plate 94 to the panel by way of a stem 94a extending from the plate. A sheave 152 is keyed to the end of the stem 94a and coupled by way of a belt 154 with a sheave 156 driven by a motor 158 mounted on the housing panel 16.

This mounting of the manipulator plate 94, for rotation about the normally horizontal axis of the stem 94a by way of the motor 158, enables the motor to orient the plate 94 upright as shown in FIGS. 1 and 2, partially inverted as shown in FIG. 9, and fully inverted as shown in FIG. 10.

FIG. 1 shows on the left side that the sample transfer device 26 of the transfer mechanism 20 of the illustrated instrument 10 is mounted on the transport mechanism 18 by way of a mounting block 160 fixed to the slide mechanism 52. The transfer device 26 accordingly moves with the transport 18 between the different positions shown in FIGS. 1, 3, 9 and 10. The transfer device is operative in the position shown in FIG. 10, and is basically inactive when in the other positions.

With reference to FIG. 2, the illustrated transfer device 26 has an upright tubular probe 162 mounted to stand above the mounting block 160, and has an annular trough 164 concentric with the probe at its lower end and seated on the mounting block 160. The probe 162 has a central fluid passage 162a feeding up from a port 160a in the mounting block to the probe open upper end 162b.

The illustrated probe is generally cylindrical and has an enlarged, outwardly flaring upper end 162b that supports a disk-shaped open-cell sponge 166. The sponge diameter is only slightly smaller than the inner diameter of the cylindrical wall 66 of the sample collector 22. This enables the sponge to fit within the sample collector and cover essentially the entire surface area of the screen filter 68, as shown in FIG. 10 and discussed further below. As further shown in FIG. 2, the sponge 166 is removable and replaceable on the probe upper end. The illustrated probe has a set of prongs 162c upwardly projecting from the probe rim around the upper end of the passage 162c, for seating the sponge 166 to the probe and allowing ready replacement of the sponge. As also shown in FIG. 2, the outer wall of the illustrated probe 162 tapers gradually from the enlarged sponge-supporting upper end to the smaller diameter of the probe shaft, for ensuring that excess liquid in the sponge principally flows down the outer surface of the probe to the trough and does not drip or otherwise fall freely from the sponge.

The illustrated trough 164, shown in FIG. 2, forms an annular basin around the lower end of the probe 162 for collecting liquid that drops or drains from the top of the probe, from the sponge 166, and from the sample collector 122 when it is inverted over the top of the sample transfer device, as appears in FIG. 10. The trough 164 has a drain passage that feeds to a drain port 160b in the mounting block 160.

The operation of the instrument 10 typically begins with the instrument in the initial condition shown in FIG. 2, with the transport mechanism in the initial position with the elevator 38 lowered and with the carriage 60 left-most. The cover 72 carried on the arm 122 is in the initial raised and offset position 130, shown with broken lines in FIGS. 6 and 7. The instrument is prepared for use with installation of a fresh sponge 166 on the sample transfer device 26 and installation of a fresh sample collector 22 in the holder of the transfer mechanism 20. A container 24 containing a liquid suspension of sample cells to be analyzed in liquid suspension is installed on the sample holder 64 carried on the carriage 60.

The instrument 10 typically operates with a programmable control unit 168 and with a fluid system 170, as shown in FIG. 4. The control unit 168 connects to each motor, i.e. the elevator motor 34, the trolley motor 46, the transfer motor 110, and the manipulator motor 158, for controlling the starting, stopping, direction and speed of each motor. The control unit 168 also connects to the fluid system 170 to control fluid operations with the sample collector 22. The fluid system connects to the sample collector 22 by way of two ports 72a and 72c in the cover 72 (FIGS. 5 and 7). The fluid system also connects with the probe port 160a and with the trough port 160b of the sample transfer device 26 (FIG. 2) for the controlled delivery of alcohol to the probe and for the controlled draining of liquids that the trough 164 collects.

After the instrument is prepared for operation as described above, the control unit 168 initiates operation by actuating the elevator motor 34 to raise the elevator 38 to the raised position of FIGS. 3 and 4. This operation raises the sample containing container 24 to telescopically receive the sample collector 22, as shown.

The control unit 168 halts operation of the elevator motor 34 when the elevator 38 is in the uppermost position of FIGS. 3 and 4, and advances to operate the transfer motor 110. The resultant rim-driven rotation of the sample collector 22 creates shear forces in the cell-suspending liquid within the sample container 24, which disperse the sample cells. After stopping the motor 110, the control unit operates the manipulator motor 124 to move the cover 72 to closed position of FIGS. 1 and 5.

With the sample collector 22 thus closed by the cover 72, the control unit 168 operates the fluid system 170 to first draw liquid into the collector 22 through the filter 68, for wetting the filter. The next operation applies slight pressure within the sample collector 22 to expel any liquid therein through the filter 68 and to discharge any cells that have collected on the filter 68. A further step collects cells on the filter 68 by controllably aspirating the cell suspending liquid into the sample collector 22, by applying a controlled vacuum to the sample collector. This operation draws sample liquid through the screen filter 68 and thereby collects sample cells of interest on the outer, bottom surface of the filter. This liquid-aspirating, cell-collecting operation continues until the cells collected on the filter obstruct it sufficiently to produce a selected pressure condition, which signals that a selected quantity of cells is collected.

The control unit 168 advances to the next operation, by actuating the elevator motor 34 in the reverse direction to lower the elevator 38 to the lowermost position of FIG. 1. The sample collector 22 remains mounted in the instrument transfer mechanism with a selected spatial distribution of sample cells collected on the downwardly facing surface of the screen filter 68. The next operations of the instrument 10, under control by the control unit 168, actuates the manipulator motor 158 to rotate the manipulator plate 94 from the horizontal position of FIGS. 1 and 2 to the drain position shown in FIG. 9. This rotation is illustrated as 135° counter-clockwise from the position shown in FIG. 1. In the drain position, liquid in the sample collector 22 drains downward to the cover 72 and out from a drain port 72c aperturing the cover (FIG. 7). Also, any liquid on the exterior surfaces of the sample collector 22 flows downward and collect in the trough 78 adjacent the sample collector rim 74 (FIGS. 5 and 6).

Also at this time the control unit operates the trolley motor 46 to shift the sample transfer device 26 to the right, to the position shown in FIG. 9.

On completion of the selected drain interval, the control unit 168 again operates the manipulator motor 158 to further rotate the manipulator plate 94 from the drain position of FIG. 9 to the inverted transfer position of FIG. 10. In this position, the manipulator plate is rotated a full 180° from the collection position of FIGS. 1 and 2.

Also after the drain operation, the control unit operates the manipulator motor 124 to open the cover 72 from the sample collector 22 and to rotate it to the initial displaced position, where it is removed and out of the way from the aperture seal at the top of the sample collector 22.

The next operation is to actuate the elevator motor 34 to raise the sample transfer device 26 from the lower position in FIG. 9 to the uppermost position of FIG. 10. This operation introduces the sponge 166, carried on the probe 162 into the sample collector 22 through the now open aperture seal 70, to abut the inner side of the screen filter 68, which is now facing downwardly.

As shown in FIG. 10, a microscope slide 172 is disposed adjacent the upper and outer cell-carrying side of the screen filter 68. A slide mechanism 174 can be provided for introducing the microscope slide 172, or the operation can be performed manually, by an operator.

The slide mechanism 174, FIG. 10, preferably presents a clean slide 172 to the cell-carrying filter element 68 on the inverted collection vessel 22. The slide mechanism provides clearance space for the platform 94 to invert, FIG. 9, between the opposite upright position of FIG. 3 for cell collection and the inverted position of FIG. 10 for cell transfer. A slide mechanism 174 for such automatic or semi-automatic operation with the instrument 10 can be provided with conventional skills. with reference to FIGS. 2 and 10, the instrument 10 is now ready to transfer the collected cells from the filter 68 to the microscope slide 172, by operating the fluid system 170 (FIG. 4) to flow alcohol upward in the probe passage 162 to flood the sponge 166. This application of alcohol from the sponge to the inner surface of the filter, with slight pressure, transfers cells from the filter 68 to the abutting surface of the microscope slide 172 and fixes them on the slide. The cells have essentially the identical spatial distribution on the slide as they had on the filter 68. Excess alcohol flows down the outer wall of the transfer device probe 162 and is collected in the trough 164, from which it is drained under control of the fluid system 170.

The microscope slide with the selected quantity and spatial distribution of sample cells thereon is then removed from the instrument 10, either manually or by way of the automated slide mechanism 174, and is ready for visual examination.

The instrument 10 is now ready to be prepared for another cell processing operation. The only preparation required is to remove and replace the sample collector 22 and the sample container 24. Preferably the sample transfer sponge 166 also is discarded and a fresh one installed. Further, the programmable control unit 168 operates the instrument motors to return the instrument to the initial position of FIG. 1.

Alternative to transferring collected cells for the filter element 68 to a glass slide 172 with an alcohol flow through a sponge 166 as described above with reference to FIG. 10, FIG. 11 shows an embodiment of the invention that transfers cells with a pneumatic action. The embodiment of FIG. 11 also illustrates a collection vessel 180 that mounts a filter element 182 with a bias or sloped orientation. The pneumatic cell transfer can, however, be used with the collection vessel 22 and the alcohol transfer action of FIG. 10 can correspondingly be used with a bias oriented filter element 182 as shown on the collection vessel 180 of FIG. 11.

More particularly, the collection vessel 180 has a cylindrical tubular body 184 closed at one end with a fixed cover 186. A drive and mounting rim 188 extends radially outward from the cover 186 for removably and replaceably mounting the collection vessel to an instrument, as described above with reference to FIGS. 1 through 10. The drive and mounting rim 188 shown in FIG. 11 differs from the corresponding rim 74 of the collection vessel 22 shown in FIG. 2 to illustrate that practice of the invention is not restricted to the illustrated rim 74 of FIG. 2. Similarly, the corresponding mounting and drive elements of the instrument 10 are to be modified to correspond with the rim 188.

FIG. 12 shows the collection vessel 180 in an upright orientation, with the filter element 182 lowermost and hence oriented for collecting cells in the manner described above with reference to FIG. 3. The filter element 182 closes the cylindrical body 184 at the axial end opposite from the cover 186 (FIG. 11). The dimensions and materials of the cylindrical body 189 and of the filter element 182 can be the same as those described above with regard to the collection vessel 22 (FIG. 2), with the modification that the filter element 182 is oriented along a plane extending at a slight angle from being transverse to the cylindrical axis 185 of the body 184. The illustrated filter 182 is at a thirty degree angle, by way of example, from being transverse to the axis 185.

This angled or biased orientation of the filter element 182 minimizes the likelihood that air bubbles will be trapped on the underside of the filter element when the collection vessel is in the upright orientation for cell collection, as in FIG. 12. The bias oriented filter element 182 also provides a surface for collecting cells that is larger in area than the corresponding area of a circular filter oriented transverse to the cylindrical axis as in the collection vessel 22 described above. Thus, the collection vessel 180 shown in FIGS. 11 and 12 provides a larger filter surface area for the collection of cells and hence can transfer a larger number of cells and apply cells to a correspondingly larger spot on a glass slide 190, as FIG. 11 illustrates. FIG. 12 similarly shows a projection of the enlarged eliptical surface area of the filter element 182, as designated with the numeral 182'.

A further element of the collection vessel 180 of FIGS. 11 and 12 is a conduit 192 sealed to the cover 186 and preferably located along the cylindrical axis 185. The conduit extends a short axial length outward from the vessel 180 to a rotary joint 194 (FIG. 11), and extends within the vessel for a selected length. More particularly, the conduit 180 length within the vessel 180 is sufficiently short to remain above the level of the maximal expected volume of liquid 196 aspirated into the vessel during the cell collection process, as FIG. 12 shows. Moreover, the axial length of the conduit 192 within the vessel is sufficiently long to project beyond the level of that liquid 192 when the vessel is inverted to the cell transfer position, as FIG. 11 illustrates. With this arrangement of the conduit 192, the vessel 180 can be inverted, by way of the instrument platform 94 as described above with reference to FIGS. 9 and 10, while still retaining the entire volume of aspirated liquid therein and hence without requiring draining or other opening of the vessel. The aspirated liquid simply remains within the vessel 180 and flows from the filter end of the vessel, FIG. 12, to the cover end of the vessel, FIG. 11, during the vessel inversion without any leakage outward from the vessel.

It will thus be seen that the collection vessel 180 forms a first chamber section for containing, when oriented, as in FIG. 12, with the filter element 182 vertically below the ends of conduit 192, a first volume of liquid below the conduit end. This is the volume of liquid aspirated into the vessel during the cell collection operation. Further, the same collection vessel 180 forms a second chamber section, when oriented, as in FIG. 11, with the filter element vertically above the conduit end, for containing that same first volume of liquid, again below the conduit end. The conduit 192 thus extends within the collection vessel 180 and has a conduit end located to be vertically above a first volume of liquid therein both when the vessel is oriented with the filter element lowermost and when the vessel is inverted from that orientation.

With further reference to FIG. 11, cells collected on the filter 182 are transferred to the viewing slide 190 by placing the slide contiguous with the filter element 182. One preferred orientation is with the slide element horizontal, as FIG. 11 illustrates, and with the collection vessel 180 oriented partially upright to dispose the filter element 182 in a corresponding horizontal orientation.

A pneumatic source 198, preferably under the electronic control of the programmable control unit 168 of FIG. 4, is coupled with the rotary coupling 194 on the conduit 192 by way of a connecting conduit 200. The pneumatic source applies a selected pneumatic pulse, typically of clean air, into the vessel 180 by way of the conduit 192. The resultant increased pneumatic pressure within the vessel 180 deflects the filter element 182 against the adjacent surface of the glass slide 190. Further, the pneumatic pressure dislodges the collected cells from the outer surface of the filter element 182 and urges them against the glass slide. In addition, droplets of the collection liquid that are within pores of the filter element 182 are dislodged by the pneumatic pressure and effectively blown against the glass slide, thereby wetting the slide and the transferred cells.

The graph of FIG. 13 shows that a preferred profile of the pressure pulse raises the pressure within the collection vessel 180 to a positive pressure ($p_2$), from the negative pressure value ($p_1$) remaining in the vessel after termination of the cell collecting aspiration. In one preferred embodiment, the duration of the pressure pulse, waveform 202, at the upper pressure level ($p_2$) is a matter of seconds, typically two to five seconds. The pressure value ($p_2$) is below the bubble pressure, in one illustrative instance is two psi.

Upon completion of this transfer of cells from the filter element to the glass slide, the glass slide is ready for staining and viewing. The instrument fitted with the collection vessel 180 is quickly readied for processing a further sample by removing and replacing the collection vessel 180, suitably with the aspirated sample liquid 196 therein. The conduit 192 can be sealed or capped to prevent inadvertent leakage of that liquid.

It will thus be seen that the invention efficiently attains the objects set forth above, among those made apparent from the preceding description. Since certain changes may be made in the above instrument and construction, and in carrying the above method, and in the sample collector article set forth, without departing from the scope of the invention, it is intended that all matter containing the above description or shown the accompanying drawings be interpreted as illustrative and not in a limiting sense.

It is also to be understood that the following claims are intended to cover all generic and specific features of the invention herein described, and all statements of the scope of the invention which, as a matter of language, might be said to fall therebetween.

Having described the invention, what is claimed as new and secured by Letters Patent is:

1. A method for a mechanized collection of sample cells that are in liquid suspension, for visual examination, said method comprising the steps of
   A. introducing a cell-dispersing device into the liquid suspension of cells,
   B. operating said cell-dispersing device for dispersing the sample cells,
   C. providing a filter device having a screen filter with a porosity for blocking sample cells of interest and for passing smaller particles and with a filter surface on which the blocked cells collect and from which the collected cells are subsequently transferred to a viewing device in contact with that surface,
   D. immersing said filter device in the liquid suspension of cells and directing a flow of the cell-suspending liquid through said filter device for collecting sample cells of interest on the filter surface, and
   E. withdrawing said filter device with sample cells collected thereon from the cell-suspending liquid, with a spatial distribution ready for said visual examination.

2. A method according to claim 1 in which said steps of introducing said cell-dispersing device and immersing said filter device include providing said cell-dispersing device and said filter device on a common structure, for concurrent introduction to the liquid suspension of cells.

3. A method according to claim 1 in which said step of providing said filter device provides said screen filter with said filter surface being substantially planar.

4. A method according to claim 1 in which said introducing and operating steps include introducing a rotor device into the liquid suspension of cells and rotating said rotor device relative to the liquid suspension of cells for subjecting the cells to shear forces for dispersing the sample cells.

5. A method according to claim 1
   A. in which said filter device employs a substantially planar screen filter element, and
   B. comprising the further steps of
      (i) orientating said screen filter element substantially horizontally, and
      (ii) directing the flow of cell-suspending liquid upward through said screen filter element, for collecting sample cells of interest onto a downwardly facing surface of the screen filter element.

6. A method according to claim 1 further comprising the steps of
   A. disposing the filter device with the collected cells thereon adjacent a viewing slide device,
   B. transferring the collected sample cells from the filter device to the viewing slide device, and
   C. maintaining the spatial distribution, that the collected sample cells have on the filter device, during said transfer step.

7. A method according to claim 1 further comprising the steps of
   A. providing said filter device with a substantially planar screen filter element on which the sample cells are collected from the cell suspending liquid,
   B. disposing a viewing slide device contiguously adjacent the collected sample cells on the screen filter element, and
   C. flowing a cell-transferring and fixing liquid through said screen filter element for transferring collected cells from the screen filter element onto said viewing slide device.

8. A method according to claim 1 further comprising the steps of
   A. providing said filter device with a selectively configured screen filter element on which the sample cells are collected from the cell suspending liquid,
   B. disposing a viewing slide device in adjacent face-to-face relation with the collected sample cells on the screen filter element, and
   C. applying a pneumatic pressure against said screen filter and directed toward said slide device for transferring collected cells from the screen filter element onto said viewing slide device.

9. A method according to claim 1 further comprising the steps of

A. introducing a chamber device into the liquid suspension of cells,
B. providing a tubular wall element on said chamber device for subjecting the liquid suspension of cells to shear forces, upon movement relative to the liquid suspension of cells, for effecting said dispersion of sample cells, and
C. providing said filter device as a screen filter element on said chamber device for effecting said filter device-immersion and sample cell-collection steps.

10. A method for the mechanized collection of particles from liquid suspension for examination, said method comprising the steps of
A. immersing into the particle-suspending liquid an agitating device for producing shear in the particle-suspending liquid for dispersing the particles,
B. agitatingly moving the agitating device relative to the particle-suspending liquid for producing shear forces for dispersing the particles,
C. providing a screen filter element on the agitating device for immersion in the particle-suspending liquid, said filter element having a porosity for blocking particles of interest and for passing smaller particles, and having a filter surface on which the blocked particles collect with a selected spatial distribution and from which the collected particles are transferred, with substantially the same spatial distribution, to a viewing device in contact with the filter surface, and
D. directing a flow of the particle-suspending liquid through the immersed filter element for collecting particles of interest on the filter element with a spatial distribution ready for said transfer and examination.

11. Apparatus for collecting, from a liquid suspension, a selected spatial distribution of particles, aid apparatus comprising
A. fluid-confining vessel means having
(i) vessel walls for immersion into the particle-suspending liquid and for producing shear forces in that liquid in response to agitating movement of said vessel walls relative to the liquid, and
(ii) screen filter means forming part of said vessel means and having a filter porosity to block and thereby to collect thereon particles of interest and to pass liquid and smaller particles, said filter means being disposed for the collection of particles thereon with a substantially monolayer spatial distribution,
B. means for the transfer of particles from said filter means to a viewing device contiguous therewith with said spatial distribution of the particles for visual examination, and
C. mounting means secured to said vessel means for removeably and replaceably mounting said vessel means with selected orientation and with selected disposition of said vessel walls and of said filter means.

12. Apparatus according to claim 11 in which said mounting means includes rim means secured to said vessel walls and arranged for said removable and replaceable mounting of said vessel means, said rim means being further arranged for receiving movement for providing said agitating movement of said vessel means.

13. Apparatus according to claim 11 in which
A. said vessel means is elongated along an axis of agitating movement,
B. said filter means is disposed at a first location along said axis, and
C. said mounting means is located on said vessel means along said axis distal from said filter means.

14. Apparatus according to claim 11 in which
A. said vessel means produces the shear forces in response to rotational movement about an axis and in which said vessel walls include tubular walls conforming to a surface of revolution about said axis, and
B. said filter means includes a screen filter element at least partially spanning said tubular walls and extending transversely to said axis.

15. Apparatus according to claim 14 in which said mounting means include rim means joined to said tubular walls and extending radially outwardly therefrom for removably and replaceably mounting said apparatus for said driven rotation.

16. Apparatus according to claim 11 in which said vessel means further has
A. sealing aperture means for removably and replaceably receiving a closure element with fluid-tight sealing, and
B. is fluid tight except at said sealing aperture means and at said filter means.

17. Apparatus according to claim 11
A. in which said vessel means is elongated along an axis and said filter means is disposed at a first location along said axis, and
B. further comprising conduit means extending along said axis for a selected distance within the vessel means, said conduit means extending within said vessel means from a second location distal to said first location and further extending outside said vessel means from within said vessel means.

18. Apparatus for processing particles suspended in liquid, said apparatus comprising
A. fluid-confining vessel means having
(i) vessel walls for immersion into the particle-suspending liquid, and
(ii) screen filter means forming part of said vessel means and having a filter porosity to block particles of interest and to pass liquid and smaller particles,
(iii) said vessel means being elongated along a first axis and having said filter means disposed at a first location along said axis and oriented substantially transverse thereto, and
B. conduit means extending from outside said vessel means to a conduit end disposed within said vessel means,
(i) said vessel means being arranged to be fluid tight, except at said filter means and at said conduit means,
(ii) said filter means and said conduit means providing said vessel means with a first chamber section for containing, when oriented with said filter means vertically below said conduit end, a first volume of liquid below said conduit end, and providing said vessel means with a second chamber section, when oriented with said filter means vertically above the conduit end, for containing said first volume of liquid below said conduit end.

19. Apparatus according to claim 18 in which said conduit means is arranged with said conduit end thereof being directed toward said filter means along said axis.

20. Apparatus for processing particles, including cells, suspended in liquid, said apparatus comprising
  A. a liquid containment body formed at least in part with a screen filter element through which liquid can flow into and out of said containment body, said filter element having a porosity selected to pass liquid and particles below a selected threshold size and for blocking on a filter surface particles larger than said threshold size,
  B. said filter element having said filter surface disposed for the collection thereon of blocked particles in a substantially monolayer spatial distribution and for the subsequent transfer therefrom of the collected particles to a viewing device in contact therewith, with the transferred particles having substantially the same spatial distribution,
  C. said liquid containment body being arranged for movement relative to a selected axis and relative to the particle-suspending liquid, for thereby subjecting the particle-suspending liquid to shear forces for dispersing the particles,
  D. means on said containment body for mountingly-supporting said containment body, said means being arranged for removably and replaceably mounting said body and for receiving driven movement for said movement of said body relative to said axis, and
  E. means forming a removable and replaceable fluid-tight sealing aperture on said liquid containment body.

21. Apparatus for processing particles, including cells, suspended in liquid, said apparatus comprising
  A. a liquid containment body formed at least in part with a screen filter element through which liquid can flow into and out of said containment body, said filter element having a porosity selected to pass liquid and particles below a selected threshold size and for blocking particles larger than said threshold size,
  B. said liquid containment body being arranged for agitating movement relative to a selected axis and relative to the cell-suspending liquid, for thereby subjecting the cell-suspending liquid to shear forces for dispersing the particles,
  C. means connected to said containment body for mountingly-supporting said containment body, said means being arranged for removably and replaceably mounting said body and for receiving driven movement for said agitating movement of said body relative to said axis, and
  D. conduit means extending within said liquid containment body and having a conduit end located to be vertically above a first volume of liquid therein both when said body is oriented with said filter element lowermost and when said body is inverted from that orientation.

22. Apparatus for preparing sample cells that are in liquid suspension for visual examination, said apparatus comprising
  A. a cell dispersing device and means for operating said cell dispersing device to disperse the sample cells,
  B. a screen filter device arranged for immersion in the cell-suspending liquid and having a substantially planar disposition and a porosity for blocking sample cells of interest on a planar surface thereof and for passing smaller particles, said filter device being arranged for the transfer therefrom, to a viewing device, of cells collected thereon from the liquid suspension,
  C. means for directing a flow of the cell-suspending liquid through said filter device immersed therein for collecting sample cells of interest on the filter device, and
  D. means for immersing said filter device in the cell-suspending liquid, and for withdrawing said filter device from the cell suspending liquid with sample cells collected thereon with a spatial distribution ready for said visual examination.

23. Apparatus as set forth in claim 22 wherein said cell dispersing device and said filter device form a common structure.

24. Apparatus as set forth in claim 22 wherein said filter device includes a planar screen filter element.

25. Apparatus as set forth in claim 22
  A. in which said filter device employs a substantially planar screen filter element, and
  B. further comprising
    (i) means for orientating said screen filter element to extend at least partially horizontally when immersed in the cell-suspending liquid, and
    (ii) means for directing the flow of cell-suspending liquid upward through said screen filter element, for collecting sample cells of interest onto a downwardly facing surface of the screen filter element.

26. Apparatus as set forth in claim 22 further comprising means for transferring cells, which are collected on said filter device, from said filter device to a viewing slide device with the same spatial distribution as on said filter device.

27. Apparatus as set forth in claim 22 further comprising means for flowing a cell transferring and fixing liquid through said filter device for transferring collected cells from said filter device onto a viewing slide device.

28. Apparatus as set forth in claim 22 further comprising means for selectively applying pneumatic pressure to the filter device and directed for dislodging collected cells therefrom for transferring collected cells from said filter device onto a viewing slide device.

29. Apparatus as set forth in claim 22
  A. wherein said filter device includes a substantially planar screen filter element on which the sample cells are collected from the cell suspending liquid,
  B. further comprising means for disposing said screen filter element with the surface thereof on which the sample cells are collected being in adjacent face-to-face relation with a viewing slide device,
  C. further comprising means for flowing a cell-transferring liquid upwardly through said screen filter element for transferring collected cells from the screen filter onto the viewing slide device.

30. Apparatus as set forth in claim 22
  A. wherein said filter device includes a substantially planar screen filter element on which the sample cells are collected from the cell suspending liquid,
  B. further comprising means for disposing said screen filter element with the surface thereof on which the sample cells are collected being in adjacent face-to-face relation with a viewing slide device,
  C. further comprising means for applying a selected pneumatic pressure signal to said filter element and directed toward said slide device for transferring collected cells from the screen filter element onto said viewing slide device.

31. Apparatus as set forth in claim 22 wherein said cell dispersing device includes a chamber device arranged for immersion in the cell-suspending liquid and having a wall element for subjecting the liquid suspension of cells to shear forces upon agitating movement relative to the liquid suspension of cells, for effecting said dispersion of cells and wherein said filter device is a screen filter element forming part of said chamber device.

32. Apparatus for preparing for examination sample cells in a liquid suspension, said apparatus comprising
   A. a cell-dispersing agitating device arranged for immersion into the cell-suspending liquid to produce shear forces in the cell-suspending liquid for dispersing the cells,
   B. a screen filter element on the agitating device for immersion in the cell-suspending liquid, said screen filter element having a porosity for blocking sample cells of interest and for passing smaller particles, said filter element being disposed for the collection thereon of blocked cells in a substantially monolayer spatial distribution, and for the subsequent transfer of cells therefrom to a viewing device placed substantially contiguous therewith, with the transferred cells having substantially the same spatial distribution, and
   C. means for directing a flow of the cell-suspending liquid through the immersed screen filter element for collecting sample cells of interest on said screen filter element with said spatial distribution for examination.

33. Apparatus as set forth in claim 32 wherein said agitating device includes a liquid vessel having vessel-forming walls for producing the shear forces upon agitating movement relative to the cell-suspending liquid, and wherein said screen filter element is provided on said vessel for flowing the cell-suspending liquid through said filter element and into said vessel.

34. Apparatus as set forth in claim 32 further comprising
   A. frame means arranged for supporting the liquid suspended cells,
   B. means on said frame means for removably and replaceably mounting said agitating device and movable relative to an axis, and
   C. means on said frame means for moving said agitating device, when mounted with said frame means, relative to the cell-suspending liquid for producing the cell-dispersing shear forces.

35. A method for preparing sample cells in liquid suspension for examination, said method comprising the steps of
   A. immersing into the cell-suspending liquid an agitating device for producing shear in the cell-suspending liquid for dispersing the cells,
   B. agitatingly moving the agitating device relative to the cell-suspending liquid for producing shear forces for dispersing the cells,
   C. providing a screen filter element on the agitating device for immersion in the cell-suspending liquid, said filter element having a porosity for blocking sample cells of interest and for passing smaller particles,
   D. directing a flow of the cell-suspending liquid through the immersed filter element for collecting sample cells of interest on the filter element with a spatial distribution ready for said examination,
   E. removing the filter element with sample cells collected thereon from the cell-suspending liquid,
   F. disposing the filter element adjacent a viewing slid element, and
   G. subjecting the filter element to a fluid condition for transferring the collected sample cells from the filter element to the viewing slide element with substantially the same spatial distribution.

36. Apparatus for preparing for examination sample cells in a liquid suspension, said apparatus comprising
   A. a cell-dispersing agitating device arranged for immersion into the cell-suspending liquid to produce shear forces in the cell-suspending liquid for dispersing the cells,
   B. a screen filter element on the agitating device for immersion in the cell-suspending liquid, said screen filter element having a porosity for blocking sample cells of interest and for passing smaller particles,
   C. means for directing a flow of the cell-suspending liquid through the immersed screen filter element for collecting sample cells of interest on said screen filter element with a spatial distribution ready for examination,
   D. means for removing said filter element with sample cells collected thereon from the cell-suspending liquid,
   E. means for disposing the filter element contiguously adjacent a viewing slide element, and
   F. means for transferring the collected sample cells from the filter element to the viewing slide element with substantially the same spatial distribution.

* * * * *